(12) United States Patent
Gronemann et al.

(10) Patent No.: US 11,629,111 B2
(45) Date of Patent: Apr. 18, 2023

(54) PROCESS AND PLANT FOR PRODUCING METHANOL FROM SUBSTOICHIOMETRIC SYNTHESIS GAS

(71) Applicant: L'Air Liquide, Société Anonyme pour l'Etude et l'Exploitation des Procédés Georges Claude, Paris (FR)

(72) Inventors: Veronika Gronemann, Karben (DE); Karin Huder, Frankfurt am Main (DE)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 17/549,421

(22) Filed: Dec. 13, 2021

(65) Prior Publication Data

US 2022/0185752 A1 Jun. 16, 2022

(30) Foreign Application Priority Data

Dec. 15, 2020 (EP) .................................... 20020615

(51) Int. Cl.
*C07C 29/151* (2006.01)
*B01D 53/047* (2006.01)
(Continued)

(52) U.S. Cl.
CPC ........ *C07C 29/1518* (2013.01); *B01D 53/047* (2013.01); *B01J 19/245* (2013.01);
(Continued)

(58) Field of Classification Search
CPC .... C01B 2203/0216; C01B 2203/0255; C01B 2203/0272; C01B 2203/0405;
(Continued)

(56) References Cited

U.S. PATENT DOCUMENTS 4,326,041 A  4/1982  Bahnisch
5,827,901 A  10/1998  Konig et al.
(Continued)

FOREIGN PATENT DOCUMENTS

DE      29 34 332      3/1981
DE   10 2008 049 622   4/2010
(Continued)

OTHER PUBLICATIONS

Ullmann's Encyclopedia of Industrial Chemistry, $6^{th}$ Ed. 1998 electronic release, Methanol, 5.2 Synthesis, 620-621.
(Continued)

*Primary Examiner* — Jafar F Parsa
(74) *Attorney, Agent, or Firm* — Elwood L. Haynes

(57) ABSTRACT

Proposed is a process for producing methanol from synthesis gas by means of multi-stage, for example two-stage, heterogeneously catalyzed methanol synthesis, wherein the methanol product formed in every synthesis stage is separated by condensation and the remaining residual gas is supplied to the downstream synthesis stage or after separation of a purge stream recycled to the first synthesis stage as a recycle stream. According to the invention after each synthesis stage the residual gas streams have separated from them a respective purge stream, from which, using one or more hydrogen recovery apparatuses, hydrogen is separated and recycled to the first synthesis stage. The ratio of the individual purge streams and their total molar flow may optionally be varied to allow better control of the reaction in the individual synthesis stages and to allow reaction to the advancing deactivation of the catalysts present therein.

16 Claims, 1 Drawing Sheet

(51) Int. Cl.
  *B01J 19/24* (2006.01)
  *C01B 3/24* (2006.01)
  *C01B 3/36* (2006.01)
  *C01B 3/56* (2006.01)

(52) U.S. Cl.
  CPC .................. *C01B 3/24* (2013.01); *C01B 3/36* (2013.01); *C01B 3/56* (2013.01); *B01J 2219/0004* (2013.01); *C01B 2203/0216* (2013.01); *C01B 2203/0255* (2013.01); *C01B 2203/0272* (2013.01); *C01B 2203/0405* (2013.01); *C01B 2203/061* (2013.01); *C01B 2203/1241* (2013.01)

(58) Field of Classification Search
  CPC ...... C01B 2203/061; C01B 2203/1241; C07C 29/1518; B01D 53/047

See application file for complete search history.

(56) References Cited

U.S. PATENT DOCUMENTS

| | | |
|---|---|---|
| 7,786,180 B2 | 8/2010 | Fitzpatrick |
| 11,247,954 B2 * | 2/2022 | Oelmann ................ C07C 29/16 |
| 2011/0178187 A1 | 7/2011 | Kopetsch |
| 2012/0129958 A1 | 5/2012 | Bormann et al. |
| 2012/0322651 A1 | 12/2012 | Schlichting et al. |
| 2016/0083319 A1 | 3/2016 | Hackel et al. |

FOREIGN PATENT DOCUMENTS

| | | |
|---|---|---|
| DE | 10 2010 008 857 | 8/2011 |
| EP | 0 790 226 | 8/1997 |
| EP | 1 016 643 | 7/2000 |
| WO | WO 2006 01888610 | 2/2006 |
| WO | WO 2018 153625 | 8/2018 |

OTHER PUBLICATIONS

European Search Report for corresponding EP 20020615, dated May 25, 2021.

* cited by examiner

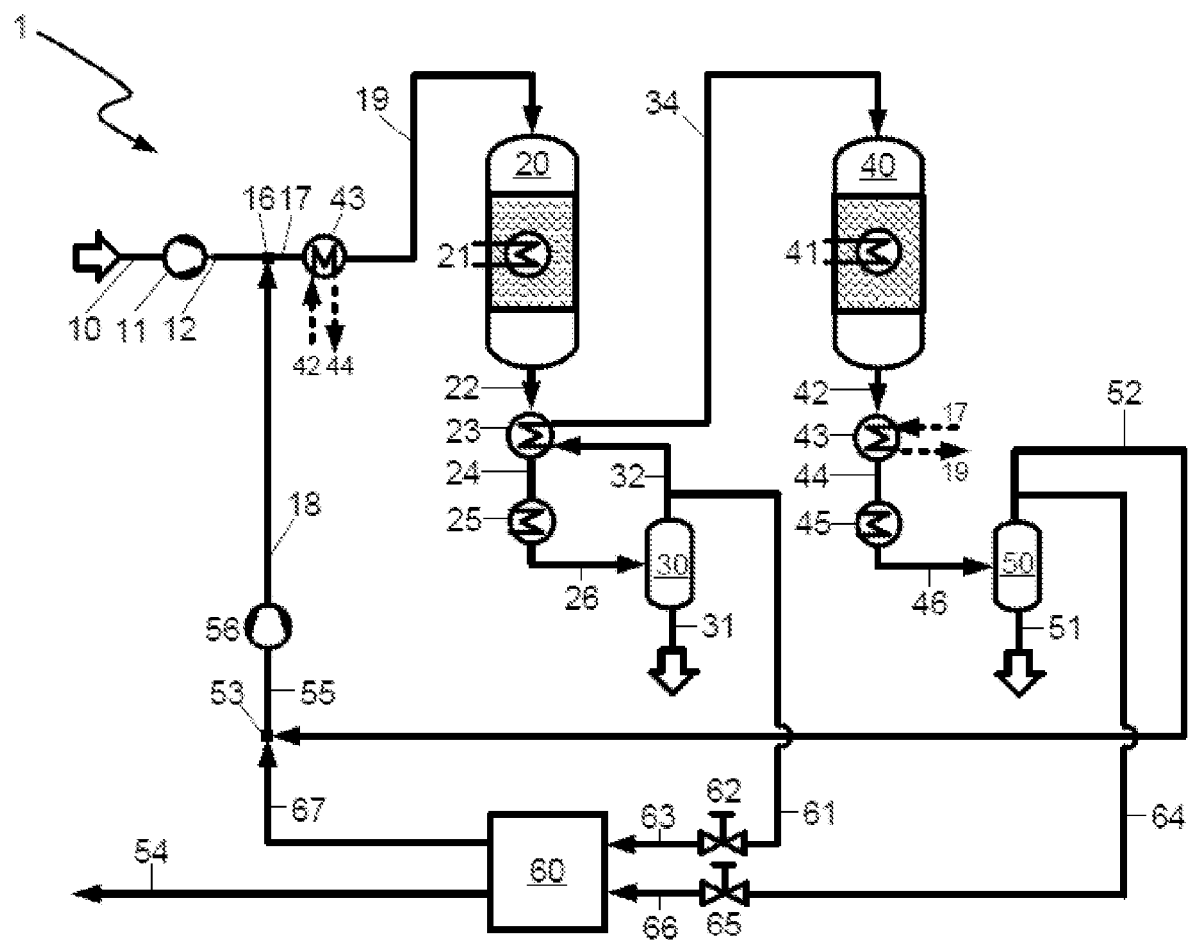

PROCESS AND PLANT FOR PRODUCING METHANOL FROM SUBSTOICHIOMETRIC SYNTHESIS GAS

CROSS REFERENCE TO RELATED APPLICATIONS

This application claims the benefit of priority under 35 U.S.C. § 119 (a) and (b) to European Patent Application No. 20020615.9, filed Dec. 15, 2020, the entire contents of which are incorporated herein by reference.

BACKGROUND

Field of the Invention

The invention relates to a process for producing methanol by heterogeneously catalyzed conversion of synthesis gas comprising hydrogen and carbon oxides having a deficiency in hydrogen in respect of the optimal stoichiometry for methanol synthesis over solid, granular catalysts for methanol synthesis arranged in a plurality of serially arranged fixed-bed reactors. The invention further relates to a plant for performing such a production process.

Prior Art

Processes for industrial production of methanol by heterogeneously catalyzed conversion of synthesis gas, i.e. mixtures of hydrogen and carbon oxides, have long been known in the art. Ullmann's Encyclopedia of Industrial Chemistry, Sixth Edition, 1998 Electronic Release, chapter "Methanol", subchapter 5.2 "Synthesis" describes various basic processes for producing methanol by catalytic conversion of synthesis gas comprising hydrogen and carbon oxides in which such reactors are employed.

A modern two-stage process for producing methanol is disclosed in European patent specification EP 0 790 226 B1 for example. The methanol is produced in a circular process wherein a mixture of fresh and partly reacted synthesis gas is supplied initially to a water-cooled reactor (WCR) and then to a gas-cooled reactor (GCR), in each of which the synthesis gas is converted over a copper-based fixed-bed catalyst to afford methanol, wherein a partial conversion is carried out in both reactors and a considerable amount of unconverted synthesis gas remains in each case. The methanol produced in the process is separated from the remaining synthesis gas to be recycled which is then passed through the gas-cooled reactor in countercurrent as coolant and preheated to a temperature of 220° C. to 280° C. before it is introduced into the first synthesis reactor. A portion of the synthesis gas to be recycled is removed from the process as a purge stream to prevent inert components such as methane from accumulating within the synthesis circuit. This measure is also taught in German laid-open specification DE 2934332 A1 and European patent application EP 1016643 A1.

The first water-cooled reactor stage typically achieves the main conversion of the synthesis gas (CO, $CO_2$, $H_2$) and removes the largest portion of the reaction heat while the second gas-cooled stage converts a nevertheless considerable portion of the synthesis gas under milder conditions.

Some multistage plant configurations for methanol synthesis additionally employ an intermediate condensation stage between the individual reaction stages to reduce the proportion of resulting reaction products (predominantly methanol and water) in the input gas for the subsequent reaction stage. This brings about not only an advantageous shift in the equilibrium position of the methanol-forming reaction in the direction of the target product methanol but also a reduction in the space velocity/increase in residence time in the subsequent reactor which likewise increases reactant conversion further. Such plant configurations are taught for example in German patent specification DE 10 2008 049 622 B4.

The water-cooled reactor (WCR) is typically a shell-and-tube reactor comprising corresponding tube plates, wherein the catalyst is filled into the tubes while cooling is effected by means of boiling water/steam generation on the shell side around the tubes. In the gas-cooled reactor (GCR) cooling is effected with the input gas which is passed through the tubes and is heated on the way to the first reaction stage (WCR) while the catalyst is filled around the tubes and the reaction takes place on the shell side of the GCR. In terms of their nominal width the reaction stages are connected with large or very large pipelines; depending on plant capacity pipe diameters of up to 1 m are possible. This is attributable above all to the large gas amounts which are recycled to the second stage (recycle gas) and admixed with the fresh gas or makeup gas, i.e. fresh synthesis gas, from synthesis gas production. After preheating in the GCR the resulting gas mixture of recycle gas and fresh gas is supplied to the first reaction stage (WCR). The recycle gas amount is typically markedly greater than the fresh gas amount and depends on the achieved conversion in the reactor section. The recycle ratio RR (RR=R/F) of recycle gas amount (R) to fresh gas amount (F) is often above 2 and in many cases even above 3.5. The lower the per-pass conversion of synthesis gas by the reactor section, the higher the recycle ratio RR required to achieve sufficient yield. This leads to a corresponding increase in the circulating gas quantity which increases the space velocity of the reactors and requires greater nominal pipe widths of the connecting pipelines and also results in an increased demand for compression energy (higher flow rate and pressure drop).

It is customary for both synthesis reactors to use the same copper-based methanol synthesis catalysts which are employed as solid, granular catalysts in fixed-bed reactors. In the described two-stage WCR-GCR process the water-cooled reactor is typically operated with a higher synthesis gas entry temperature than a water-cooled reactor in a single-stage process for methanol synthesis in order to allow provision of higher-pressure steam. This reactor is further provided with synthesis gas that is not yet fully reacted. The high exothermicity of the methanol synthesis therefore requires very good temperature control of the reactor to avoid overheating of the catalyst which contributes substantially to premature deactivation thereof. German laid-open specification DE 102010008857 A1 therefore proposes using catalysts having different activities in the two synthesis reactors, wherein the reactor having the more drastic reaction conditions is to employ a catalyst of lower activity having a lower deactivation rate and thus higher long-term stability.

There are different processes for producing synthesis gas comprising hydrogen and carbon oxides as input gas for methanol synthesis, for example steam reforming, autothermal reforming (ATR), combinations thereof (so-called combined reforming) and noncatalytic partial oxidation (POX). Suitable starting materials are hydrocarbons such as natural gas having a main component of methane or naphtha. The recited processes afford different ratios of the product components carbon monoxide (CO) and hydrogen ($H_2$), as is apparent from the following reaction equations:

$$2CH_4+O_2=2CO+4H_2 \text{(partial oxidation)}$$

$$2CH_4+\tfrac{1}{2}O_2+H_2O=2CO+5H_2 \text{(autothermal reforming)}$$

$$2CH_4+2H_2O=2CO+6H_2 \text{(pure steam reforming)}$$

Since partial oxidation or autothermal reforming is operated with an excess of hydrocarbon/deficiency of oxygen to inhibit the total oxidation of the hydrocarbon to carbon dioxide, the synthesis gas obtained often has a hydrogen deficit having regard to its use as input gas for methanol synthesis. This necessitates according to the following reaction equation $$2H_2+CO \rightleftharpoons CH_3OH$$

an $H_2/CO$ ratio of at least 2 and under practical synthesis conditions often even slightly greater than 2, for example 2.1. This ratio is typically formulated as the stoichiometry number SN of the methanol synthesis and takes into account that carbon dioxide too reacts to afford methanol:

$$SN=([H_2]-[CO_2])/([CO]+[CO_2]) \geq 2 \text{(e.g. 2.1)}$$

By contrast, synthesis gases obtained by partial oxidation or autothermal reforming often have a stoichiometry number of ≤1.9, occasionally even ≤1.7. A synthesis gas having a hydrogen deficit in respect of methanol synthesis can be adapted to the required hydrogen content using the CO conversion reaction $$CO+H_2O \rightleftharpoons CO_2+H_2$$

but this has the disadvantage that an additional process step is required which results in elevated capital and operating costs and also increased emissions of climate-damaging carbon dioxide. It would therefore be more desirable to provide an input gas having the stoichiometry optimal for methanol synthesis directly via the synthesis gas production process or by adaptation of the methanol synthesis itself.

Such an adaptation of the methanol synthesis may consist of recovering unconverted hydrogen and recycling it into the synthesis. As indicated hereinabove, passage of the synthesis gas through a methanol synthesis reactor in each case achieves only partial conversion into methanol and there remains a significant proportion of unconverted synthesis gas (so-called residual gas) which is supplied as recycle gas to the methanol synthesis reactor or supplied as input gas to a further downstream methanol synthesis reactor. Prior to its further use the residual gas stream has a proportion separated from it as a purge stream. This purge stream contains not only inert components but also hydrogen and carbon oxides as unconverted synthesis gas constituents. It can therefore be used to improve the stoichiometry number of the synthesis gas when prior to its recycling to the methanol synthesis an enrichment of its hydrogen content/a depletion both of the inert components and the content of carbon oxides is carried out. This may be carried out using a hydrogen recovery apparatus which operates according to the principle of pressure swing adsorption (PSA) and/or the principle of membrane separation, to which the purge stream is supplied in part or in full. Such a concept is described for example in patent publications U.S. Pat. No. 7,786,180 B2 or WO 2018/153625 A1.

When establishing an optimized hydrogen content in the reactor feed streams it must further be taken into account that the amounts and compositions of the product gas streams discharged from the methanol synthesis reactors are subject to continual change which is attributable to the advancing deactivation of the catalysts present in the reactors over time which results in a decreasing average conversion in the respective reactor over time. Accordingly, processes having a plurality of synthesis reactions arranged in series generally initially undergo advancing deactivation of the catalyst in the first reactor in the flow direction before, at a later juncture, the catalyst activity of the catalyst in the downstream second reactor also falls. This is countered inter alia by altering the recycle ratio over time.

Both the advancing catalyst deactivation over time and the altering of the recycle ratio over time therefore necessitate continual adapting of the hydrogen content in the reactor feed streams over time. However, the abovementioned publications do not provide a solution to this. There is therefore a need for a correspondingly modified process and plant which account for these phenomena and make it possible to achieve methanol production with continually optimized composition of the reactor feed streams.

SUMMARY

It is accordingly an object of the present invention to specify a process and plant which does not exhibit the described disadvantages of the prior art and which especially makes it possible in a multistage process/a multistage plant for methanol synthesis having a plurality of serially connected synthesis reactors to ensure methanol production with continually optimized composition of the reactor feed streams.

A fluid connection between two regions of the apparatus of the invention is to be understood as meaning any type of connection which makes it possible for a fluid, for example a gas stream, to be able to flow from the one region to the other of the two regions, regardless of any regions or components located in between. In particular, a direct fluid connection is to be understood as meaning any type of connection which makes it possible for a fluid, for example a gas stream, to flow directly from one to the other of the two regions, with no further regions or components being interposed, with the exception of purely transportational operations and the means required for this purpose, for example pipes, valves, pumps, compressors, reservoirs. One example would be a pipe leading directly from one to the other of the two regions.

Synthesis gas production conditions and methanol synthesis conditions are to be understood as meaning the process conditions known per se to a person skilled in the art, in particular of temperature, pressure and residence time, as discussed in detail in the relevant literature and under which at least partial conversion but preferably industrially relevant conversions of the respective reactants into the products synthesis gas and/or methanol take(s) place. Accordingly, a catalyst active for methanol synthesis is to be understood as meaning a catalyst which brings about precisely such conversions under methanol synthesis conditions. Necessary adjustments of these conditions to the respective operational requirements will be made by those skilled in the art on the basis of routine experiments. Any specific reaction conditions disclosed may serve here as a guide, but they should not be regarded as limiting in relation to the scope of the invention.

For the purposes of this description steam is to be understood as being synonymous with water vapor unless the opposite is indicated in an individual case. By contrast, the term "water" refers to water in the liquid state of matter unless otherwise stated in an individual case.

A carbon-containing input stream is to be understood as meaning any input material streams containing carbon in elemental or chemically bonded form, generally in organically chemically bonded form, wherein it is possible to convert this carbon present under synthesis gas production conditions into a synthesis gas containing carbon oxides and hydrogen. Examples of carbon-containing material streams often employed for synthesis gas production include natural gas, naphtha, heavy fuel oil, high-boiling refinery residues, pyrolysis oils or pyrolysis tar from biomass, coal of varying qualities, particle size and coalification.

A further purification, conditioning or processing step of the raw synthesis gas is to be understood as meaning any measure or process step known from the prior art for producing a pure synthesis gas, pure hydrogen and/or pure carbon monoxide. These include CO conversion for increasing the hydrogen proportion in the synthesis gas, separation of carbon dioxide by means of a suitable scrubbing process, for example the Rectisol process, or scrubbing with amine-containing scrubbing media, cryogenic gas fractionation for producing pure carbon monoxide, pressure swing adsorption (PSA) for producing pure hydrogen, and physical process steps, for example cooling, condensing and separating the condensate.

For the purposes of the present invention, a means is something which makes it possible to achieve, or is helpful in achieving, an objective. In particular, means for carrying out a particular process step are all physical objects which a person skilled in the art would take into consideration in order to be able to carry out this process step. For example, a person skilled in the art will consider means of introducing or discharging a material stream to include all transporting and conveying apparatuses, i.e. for example pipelines, pumps, compressors, valves and the corresponding openings in container walls which seem necessary or sensible to said skilled person for performance of this process step on the basis of his knowledge of the art.

Catalytic activity or catalyst activity, especially in connection with different catalytic activities when comparing two different catalysts, is to be understood as meaning the achieved degree of conversion per unit length of the catalyst bed of reactants to products. Activity is influenced by the chemical composition, doping, poisoning, available surface area etc. of the catalyst material but also by the geometry of the catalyst particles and textural parameters of the catalyst bed, for example its porosity or packing density. Due to the exothermicity of the reactions considered, a high catalytic activity correlates with a high evolution of heat per unit length of the catalyst bed. The molar flow of liquid products collected after each catalyst stage by condensation constitutes a further measure of catalyst activity under specified methanol synthesis conditions since the reaction products of the methanol synthesis reaction according to the conversion equations $$CO\ (g) + 2H_2\ (g) = CH_3OH\ (l)$$

$$CO_2\ (g) + 3H_2\ (g) = CH_3OH\ (l) + H_2O\ (l)$$

are liquid under ambient conditions. Accordingly the parameter "activity loss" describes the decrease over time of catalyst activity and degree of reactant conversion/methanol yield as a measure for the deactivation of the catalyst.

The average catalyst activity per catalyst bed or reactor is to be understood as meaning the catalyst activity averaged not only in time (over a time period) but also in space (over the length of the catalyst bed) in the catalyst bed or reactor under consideration.

A first/second methanol synthesis reactor is not necessarily to be understood as meaning individual reactors but rather this term may also comprise respective groups of individual reactors which in turn may contain one or more catalyst zones, i.e. regions filled with solid, granular methanol synthesis catalyst. The terms "first" and "second" methanol synthesis reactor are thus merely to be understood as indicating the traversal sequence of the reactors under consideration having regard to the feed stream. The first/second methanol synthesis reactor need not necessarily follow one another in direct succession but rather may have further methanol synthesis reactors not considered in detail here arranged between them.

A catalyst cycle is to be understood as meaning the operating duration of one batch of a methanol synthesis catalyst, beginning with the startup of the methanol synthesis operation in the methanol synthesis reactor filled with the batch of fresh or regenerated methanol synthesis catalyst and terminating with the shutdown of the methanol synthesis operation in the same methanol synthesis reactor for purposes of catalyst replacement or performing a catalyst regeneration.

In the context of the present invention, separating or dividing a material stream is to be understood as meaning producing at least two substreams from one starting stream. Dividing produces at least two homogeneous, monophasic substreams from the starting stream, wherein both substreams have the same composition of matter as the starting stream. By contrast, separating comprises producing the at least two substreams using a substance separation step from the field of thermal process engineering, i.e. for example using a phase equilibrium, for example in evaporation, distillation, crystallization or membrane separation, in order that the at least two substreams generally have compositions and/or phase proportions which differ from one another and from the starting stream.

A temperature measuring apparatus is in particular to be understood as meaning corresponding measurement apparatuses which make it possible to follow the change over time of the axial temperature profile in a catalyst bed. Examples thereof would be an axially movable thermocouple or a fixedly mounted multi-point thermocouple arranged axially in the catalyst bed.

The indication that a material stream is directly supplied to a specific process stage or a specific plant part or is directly introduced into the respective process stage or plant part is to be understood as meaning that the material stream is introduced to this process stage or this plant part without previously having been passed through other process stages or plant parts with the exception of purely transportational operations and the means required therefor, for example pipelines, valves, pumps, compressors, reservoirs.

Methanol is one of the most important petrochemical products produced worldwide. The process for producing methanol may be subdivided into three main sections: Synthesis gas production (including synthesis gas treatment, if required), methanol synthesis and methanol distillation.

A number of the modern efficient processes for producing synthesis gas can result in a substoichiometric synthesis gas composition, i.e. to a synthesis gas having a hydrogen deficit and a stoichiometry number of less than 2. In order to increase the stoichiometry number to the required 2 or higher, according to the invention the substoichiometric synthesis gas is admixed with hydrogen obtained from the purge gas of the gas circuit of the methanol synthesis via one or more specific hydrogen recovery apparatuses to obtain the so-called makeup gas (referred to in the context of the present disclosure as synthesis gas input stream).

In prior art processes the purge gas proportion separated from the circuit typically remains largely constant over time, yet the purge gas molar flow and thus the molar flow of the hydrogen separated from the purge gas increases with decreasing catalyst activity from the beginning of a catalyst cycle (start of run, SOR) towards the end of the catalyst cycle (end of run, EOR). Since the specific hydrogen demand required for adjusting the desired stoichiometry number of the synthesis gas remains constant over time, there is formed over the lifetime of the catalyst an excess of hydrogen which according to the prior art is supplied to the fuel gas system and is thus only thermally and not materially recovered. It is therefore an objective of the present invention to provide a tailored hydrogen stream to establish the stoichiometry number of the synthesis gas over the lifetime of the catalyst. According to the invention this is achieved by serially arranging in customary plants for methanol synthesis at least two synthesis reactors each having one or more catalyst beds per reactor. Often also carried out between the individual synthesis reactors is a separation of the methanol produced by condensation, wherein the remaining residual gas is supplied to the subsequent synthesis reactor or recycled to the first synthesis reactor. From these residual gases a proportion may therefore in each case be removed from the synthesis circuit as purge gas and supplied to one or more hydrogen recovery apparatuses. It must be taken into account that the deactivation of the catalysts present in the synthesis reactors usually advances in the flow direction and this phenomenon is observed in a single catalyst bed under observation as well as over a plurality of serially arranged catalyst beds. In a synthesis facility having two synthesis reactors arranged in series, deactivation phenomena are therefore first observed in the first synthesis reactor in the flow direction and only subsequently observed in the second synthesis reactor in the flow direction.

The conversion in the individual synthesis reactors/methanol reaction steps changes with decreasing catalyst activity over the lifetime of the catalyst. The activity of the catalyst is influenced via process parameters, catalyst aging and poisoning of active catalyst centers. The gas composition of the separated gas phase supplied to the individual reaction stages thus varies over the lifetime of the catalyst as well as the amount of the separated purge gas while the specific hydrogen demand for adapting the stoichiometry number of the defined synthesis gas is constant. The proportions of the purge gas streams separated from the gas phase after each methanol separation stage and passed to one or more hydrogen recovery apparatuses are therefore adjusted, and varied over time, such that the required hydrogen amount for establishing the desired stoichiometry number of the synthesis gas is achieved.

The invention thus has the advantage that during most time intervals of the operating duration of the methanol synthesis plant a tailored hydrogen molar flow for establishing the stoichiometry number can be established, wherein the inventive varying over time of the at least two purge streams passed to the hydrogen recovery apparatus or apparatuses makes it possible to react to changes over time in the activity of the catalysts in the plurality of serially arranged synthesis reactors. This accordingly makes it possible to realize a relatively high hydrogen content at SOR conditions with a low purge gas stream and a relatively low hydrogen content at EOR conditions with a relatively high purge gas stream.

In a second aspect the process according to the invention is characterized in that the hydrogen-enriched supplementary stream is mixed with the synthesis gas input stream and/or with the recycle stream before introduction into the first methanol synthesis reactor. This ensures that the reactor entrance of the synthesis reactor first in the flow direction is supplied with a homogeneous gas mixture and the formation of inhomogeneities, for example local concentration streaks, is avoided.

In a third aspect the process according to the invention is characterized in that the first purge stream and the second purge stream are introduced into a common hydrogen recovery apparatus. This allows the hydrogen recovery to be carried out in a particularly economic fashion and capital and operating costs and energy consumption are reduced compared to the use of two separate hydrogen recovery apparatuses. The use of a common hydrogen recovery apparatus further results in a more homogeneous constitution of the hydrogen-enriched supplementary stream recycled to the first synthesis reactor.

In a fourth aspect the process according to the invention is characterized in that the hydrogen recovery apparatus operates according to the principle of pressure swing adsorption (PSA) and/or according to the principle of membrane separation. Both processes for hydrogen recovery and their respective process conditions are known in principle to those skilled in the art. The combination of both processes too is possible and may bring advantages compared to the individual processes.

In a fifth aspect the process according to the invention is characterized in that the ratio of the molar flows n1s/n2s of the first purge stream n1s to the second purge stream n2s is altered overtime. This allows the stoichiometry number for the synthesis gas passed to the first synthesis reactor to be adjusted to the target value of at least 2 in each case.

In a sixth aspect the process according to the invention is characterized in that the ratio of the molar flows n1s/n2s of the first purge stream n1s to the second purge stream n2s is altered over time and/or in that the sum of the first purge stream and the second purge stream n1s+n2s is altered over time. This makes it possible to react to the changing catalyst activity over time in the at least two serially arranged synthesis reactors and adjust the stoichiometry number for the synthesis gas passed to the first synthesis reactor to the target value of at least 2 in each case.

In a seventh aspect the process according to the invention is characterized in that the process is performed at a ratio of the molar flows (n1s/n2s)1 during a first time interval t1 and at a ratio of the molar flows (n1s/n2s)2 during a second time interval t2, wherein the average catalyst activity of the catalyst in the first methanol synthesis reactor is higher during the first time interval than during the second time interval. This makes it possible to react to the changing catalyst activity over time in the at least two serially arranged synthesis reactors over the time intervals t1 and t2 and adjust the stoichiometry number for the synthesis gas passed to the first synthesis reactor to the target value of at least 2 in each case by establishing a ratio of the molar flows (n1s/n2s)1 in the first time interval t1 and a ratio of the molar flows (n1s/n2s)2 during a second time interval t2. The division of the operating duration of the synthesis gas plant into two time intervals is only exemplary and is not to be understood as limiting. It may well be useful to define further time intervals t3, t4 etc. during which further molar flow ratios (n1s/n2s)3, (n1s/n2s)4 etc. are established to allow particularly incremental adjustment of the desired stoichiometry number. However, it should be ensured that the greater control complexity remains acceptable in view of the improved adjustment of the stoichiometry number.

In an eighth aspect the process according to the invention is characterized in that the process is performed at a ratio of the molar flows (n1s/n2s)1 during a first time interval and at a ratio of the molar flows (n1s/n2s)2 during a second time interval, wherein (n1s/n2s)1 is greater than (n1s/n2s)2. During the first time interval beginning with the startup of the process/the plant, fresh catalyst is present in each case in the first and in the second methanol synthesis reactor. The hydrogen present in the first reactor feed stream is therefore largely converted in the first methanol synthesis reactor and a comparatively large molar flow of the first purge stream must be passed to the hydrogen recovery apparatus to obtain a certain hydrogen amount. By contrast, during the subsequent second time interval the catalysts present in the methanol synthesis reactors are already partially deactivated; the reaction is therefore increasingly shifted from the first to the downstream second methanol synthesis reactor. There is therefore more unconverted hydrogen available at the exit of the first methanol synthesis reactor and the molar flow of the first purge stream passed to the hydrogen recovery apparatus can therefore be reduced.

In a ninth aspect the process according to the invention is characterized in that the first time interval t1 begins with the startup of the process and in that the second time interval t2 ends with the shutdown of the process. Since in the first and second methanol synthesis reactor the catalyst activity upon startup of the process is high and before shutdown of the process is relatively low due to the at least partial deactivation, marked changes in the gas compositions occur between these two time intervals at the exit of the first and second methanol synthesis reactor with the result that it is useful to track the ratio of the molar flows (n1s/n2s).

In a tenth aspect the process according to the invention is characterized in that the beginning of the first time interval t1 corresponds to the beginning of the catalyst cycle in all methanol synthesis reactors (SOR) and in that the end of the second time interval t2 corresponds to the end of the catalyst cycle in all methanol synthesis reactors (EOR). The advantages are the same as those elucidated in connection with the ninth aspect of the invention.

In an eleventh aspect the process according to the invention is characterized in that the ratio of the molar flows (n1s/n2s)1 is greater than 1 and in that the ratio of the molar flows (n1s/n2s)2 is less than 1. This reflects the finding that during the first time interval a comparatively large molar flow of the first purge stream is passed to the hydrogen recovery apparatus to obtain a certain hydrogen amount, wherein n1s is greater than n2s. During the second time interval the majority of the reaction is shifted to the second methanol synthesis reactor, the first purge stream may be reduced and the ratio (n1s/n2s)2 falls to less than 1.

In a twelfth aspect the process according to the invention is characterized in that the ratio of the molar flows (n1s/n2s)1 is between 1 and 3, preferably between 2 and 2.9, most preferably between 2.5 and 2.8, and in that the ratio of the molar flows (n1s/n2s)2 is between 0 and 1, preferably between 0.3 and 0.9, most preferably between 0.4 and 0.7. Investigations and calculations have shown that these ranges are particularly advantageous and in particular make it possible to realize a stoichiometry number of more than 2 and an advantageous recycling ratio RR.

In a thirteenth aspect the process according to the invention is characterized in that the reduction in the molar flow of the first liquid product stream serves as a measure for the reduction in catalyst activity of the catalyst in the first methanol synthesis reactor. This allows the intermediate condensation and separation of the methanol product after every synthesis reactor to be advantageously utilized for activity determination of the catalyst in this reactor since the progress over time of product amount per reactor is directly measurable via the molar flow of the collected condensed products, thus rendering costly and inconvenient gas analyses and flow measurements unnecessary.

In a fourteenth aspect the process according to the invention is characterized in that a temperature measurement apparatus is used to repeatedly measure during performance of the process axial temperature profiles within the catalyst bed in the first methanol synthesis reactor and in that the change in the axial temperature profile over time serves as a measure for the decrease in catalyst activity of the catalyst in the first methanol synthesis reactor. Suitable temperature measurement apparatuses include single-point or multi-point thermocouples which are each arranged parallel to the longitudinal axis of the catalyst bed and are arranged in the interior thereof, preferably in the center thereof. Single-point thermocouples are usually introduced into the catalyst bed in an axial guide tube and are displaceable therein so that incremental pulling out at fixed timings allows measurement of the temperature at particular positions in the catalyst bed, thus affording an axial temperature profile for a particular operating juncture. Multipoint thermocouples are fixedly arranged in the catalyst bed and measure the temperature at various axial positions of the catalyst bed at particular junctures, thus also making it possible in this way to obtain axial temperature profiles in the catalyst bed as a function of the operating time of the synthesis reactor. The strong exothermic heat evolution of the methanol synthesis reaction allows both options to provide information about the progress of the reaction and the advancing of the catalyst deactivation over time.

In a fifteenth aspect the process according to the invention is characterized in that the synthesis gas production process comprises a noncatalytic partial oxidation (POX) and/or an autothermal reforming (ATR). Since partial oxidation or autothermal reforming is operated with an excess of hydrocarbon/deficiency of oxygen to inhibit the total oxidation of the hydrocarbon to carbon dioxide, the synthesis gas obtained often has a hydrogen deficit having regard to its use as input gas for methanol synthesis. The process according to the invention for methanol synthesis thus provides particular advantages in these synthesis gas production processes and allows the respective hydrogen deficit to be efficaciously compensated.

In a sixteenth aspect the process according to the invention is characterized in that the stoichiometry number of the synthesis gas input stream is less than 2 and in that the stoichiometry number of the gas mixture obtained from the synthesis gas input stream, the recycle stream and the supplementary stream is more than 2 before introduction thereof into the first methanol synthesis reactor. As elucidated hereinabove, synthesis gases having a stoichiometry number below 2 are often obtained when the synthesis gas production process comprises a noncatalytic partial oxidation (POX) and/or an autothermal reforming (ATR). The process according to the invention for methanol synthesis thus provides particular advantages in these synthesis gas production processes and allows the respective hydrogen deficit to be efficaciously compensated.

In a further aspect the process according to the invention is characterized in that the process also comprises a third methanol synthesis reactor from whose reactor product stream a further residual gas stream containing unconverted synthesis gas constituents is obtained, wherein a further purge stream which is supplied to a hydrogen recovery apparatus is obtained from the further residual gas stream. This allows even finer reaction to the advancing catalyst deactivation in the serially arranged synthesis reactors than when only two synthesis reactors are present. By contrast, the provision of more than three synthesis reactors is usually not sensible on account of the elevated capital and operating costs.

In a further aspect the process according to the invention is characterized in that the first methanol synthesis reactor is in the form of a water-cooled reactor (WCR) and the second methanol synthesis reactor is in the form of a water-cooled reactor (WCR) or a gas-cooled reactor (GCR), wherein the first reactor feed stream is passed as cooling gas through the second, gas-cooled methanol synthesis reactor and thus heated against the second reactor product stream in indirect heat exchange prior to introduction into the first, water-cooled methanol synthesis reactor. The gas-cooled reactor thus fulfils two functions, namely as a synthesis reactor and as a heat exchanger/feed preheater for the WCR. Good temperature control of the synthesis reactors through inventive control of the course of the reaction even during increasing catalyst deactivation is therefore particularly important in the embodiment according to the WCR-GCR concept.

In a further aspect the process according to the invention is characterized in that the second methanol synthesis reactor is in the form of a gas-cooled reactor (GCR), wherein the first reactor feed stream is passed through the second, gas-cooled methanol synthesis reactor in cocurrent with the second reactor product stream and thus heated against the second reactor product stream in indirect heat exchange.

BRIEF DESCRIPTION OF THE DRAWINGS

Developments, advantages and possible applications of the invention are also apparent from the following description of working and numerical examples and the drawings. All features described and/or depicted, either in themselves or in any combination, form the invention, regardless of the way they are combined in the claims or the back-references therein.

FIG. 1 shows a schematic representation of the process/the plant according to an exemplary embodiment of the invention.

DETAILED DESCRIPTION OF PREFERRED EMBODIMENTS

In the exemplary embodiment shown in FIG. 1 of a process 1/a plant 1 according to the invention which comprises two serially arranged, water-cooled synthesis reactors 20, 40 for methanol synthesis, a fresh synthesis gas stream containing hydrogen, carbon monoxide and carbon dioxide and having a stoichiometry number of less than 2 is introduced from a synthesis gas production plant (not shown), for example a POX plant or an ATR plant, via conduit 10, compressed to synthesis pressure using compressor 11 and via conduit 12 as a synthesis gas input stream (also known as fresh gas or makeup gas) passed to mixing apparatus 16 and therein combined with a recycle stream supplied via conduit 18 and likewise introduced into the mixing apparatus 16. The mixing apparatus 16, as well as the mixing apparatuses recited hereinbelow, may be in the form of a pipe T-piece or a static mixer for example. The ratio of the molar flows passed via the conduits 18 (recycle stream) and 12 (fresh gas) to the mixing apparatus 16 corresponds to the recycle ratio RR.

The combining and mixing of the synthesis gas input stream with the recycle stream affords a first reactor feed stream which is passed via conduit 17 to heat exchanger 43 and therein heated to the reactor entry temperature for example in indirect heat exchange with the hot reactor product stream from the second synthesis reactor 40 (indicated by the dashed conduits 42, 44). Said stream is then introduced via conduit 19 into the first methanol synthesis reactor 20.

Partial conversion of the first reactor feed stream is carried out under methanol synthesis conditions in the first methanol synthesis reactor 20 which contains at least one catalyst zone comprising a solid, granular catalyst active for methanol synthesis. In the exemplary embodiment of FIG. 1 both synthesis reactors 20, 40 are water-cooled; the respective cooling apparatuses integrated into the reactors are indicated by reference numerals 21, 41. Other heat integration and cooling concepts are also possible (but not shown); the first reactor feed stream may also be utilized as a cooling gas stream in one of the reactors (GCR) as proposed by the process according to patent specification EP 0 790 226 B1. The other methanol synthesis reactor is cooled with cooling water (WCR), for example.

A hot first reactor product stream is discharged from the first synthesis reactor 20 via conduit 22 and passed to heat exchanger 23 and then, via conduit 24, to cooler 25. Heat exchanger 23 carries out a first cooling of the hot first reactor product stream by indirect heat exchange with the cooled residual gas stream discharged from the first phase separation apparatus 30. Cooler 25 may be embodied for example as an air cooler or as a cooler operated with cooling water. The first reactor product stream cooled below its dew point is introduced via conduit 26 into a first phase separation apparatus 30 and therein separated into a first liquid product stream and into a first residual gas stream. The first liquid product stream containing substantially methanol and water is discharged from the process/from the plant via conduit 31 and supplied to a crude methanol workup (not shown) which comprises for example one or preferably two or more distillation steps. The first residual gas stream containing as yet unconverted synthesis gas constituents and inert gas constituents in the context of methanol synthesis, for example methane, is passed via conduit 32 to heat exchanger 23 and therein heated in indirect heat exchange with the hot first reactor product stream from the methanol synthesis reactor 20. Subsequently the now heated first residual gas stream is via conduit 34 passed to and introduced into the second methanol synthesis reactor 40 which likewise contains at least one catalyst zone comprising a solid granular catalyst active for methanol synthesis. The second methanol synthesis reactor carries out the partial conversion of the second reactor feed stream under methanol synthesis conditions.

A hot second reactor product stream is discharged from the second methanol synthesis reactor 40 via conduit 42 and passed to heat exchanger 43 and then, via conduit 44, to cooler 45. Heat exchanger 43 carries out a first cooling of the hot second reactor product stream, for example by indirect heat exchange with the first reactor feed stream provided via conduit 17 and discharged via conduit 19 (both conduits 17, 19 indicated with dashed lines). Cooler 45 may likewise be embodied for example as an air cooler or as a cooler operated with cooling water. The second reactor product stream cooled below its dew point is introduced via conduit 46 into a second phase separation apparatus 50 and therein separated into a second liquid product stream and into a second residual gas stream. The second liquid product stream which in turn contains substantially methanol and water is discharged from the process/from the plant via conduit 51 and supplied to the crude methanol workup (not shown). The second residual gas stream containing as yet unconverted synthesis gas constituents is passed as a recycle stream via conduit 52 to mixing apparatus 53.

According to the invention downstream of the first phase separation apparatus 30 a substream of the first residual gas stream is discharged from conduit 32 via conduit 61 as a first purge stream and downstream of the second phase separation apparatus 50 a substream of the second residual gas stream is discharged from conduit 52 via conduit 64 as a second purge stream. The ratio of the first and second purge streams discharged via conduits 61 and 64 and the total molar flow resulting from the sum of both purge streams may be adjusted by means of the control valves 62 and 65. Subsequently the first purge stream and the second purge stream are supplied and introduced to a common hydrogen recovery apparatus 60 via conduits 63 and 66 respectively. This allows the hydrogen recovery to be carried out in a particularly economic fashion and capital and operating costs and energy consumption are reduced compared to the use of two separate hydrogen recovery apparatuses. The use of a common hydrogen recovery apparatus further results in a more homogeneous constitution of the hydrogen-enriched supplementary stream recycled to the first synthesis reactor.

The hydrogen recovery apparatus can operate for example according to the principle of pressure swing adsorption (PSA) and/or according to the principle of membrane separation. Both processes for hydrogen recovery and their respective process conditions are known in principle to those skilled in the art. The combination of both processes too is possible and may bring advantages compared to the individual processes. Especially when using a PSA plant as the hydrogen recovery apparatus, the use of a common hydrogen recovery apparatus affords advantages in terms of saving capital costs and reducing space requirements.

The hydrogen recovery apparatus 60 separates the first purge stream and the second purge stream into a hydrogen-enriched supplementary stream which is discharged via conduit 67 and into a hydrogen-depleted third purge stream which is discharged from the process via conduit 54 and sent for offgas disposal or offgas recovery (not shown). Discharging the third purge stream from the process efficaciously avoids accumulation of inert gases in the circuit of the methanol synthesis. In the context of methanol synthesis these include nonreactive gases, for example noble gases or methane.

The hydrogen-enriched supplementary stream discharged from the hydrogen recovery apparatus via conduit 67 is combined with the recycle stream supplied via conduit 52 in the mixing apparatus 53 which may be for example a static mixer or a simple pipe T-piece. This affords a recycle stream enriched in hydrogen which via conduit 55 is passed to and introduced into a compressor 56. The compressed recycle stream enriched in hydrogen is via conduit 18 discharged from compressor 56 and introduced into mixing apparatus 16, thus affording a first reactor feed stream enriched in hydrogen which now has a stoichiometry number of more than 2, for example 2.1.

In further examples (not shown) it is possible to initially mix the hydrogen-enriched supplementary stream discharged from the hydrogen recovery apparatus via conduit 67 with the synthesis gas input stream or with the recycle stream and the synthesis gas input stream before the obtained gas mixture is introduced into the first synthesis reactor as hydrogen-enriched, first reactor feed stream.

The inventive recovery of hydrogen from the first and second purge stream, the recycling of the recovered hydrogen to the first synthesis reactor and optionally the variation of the first and second purge stream over time result in the following advantages which are elucidated below by way of example in conjunction with FIG. 1.

In one example the ratio of the molar flows n1s/n2s of the first purge stream n1s to the second purge stream n2s is altered over time. This allows the stoichiometry number for the synthesis gas passed to the first synthesis reactor to be adjusted to the target value of at least 2 in each case.

In a further example the ratio of the molar flows n1s/n2s of the first purge stream n1s to the second purge stream n2s is altered over time and/or the sum of the first purge stream and the second purge stream n1s+n2s is altered over time. This makes it possible to react to the changing catalyst activity over time in the at least two serially arranged synthesis reactors and adjust the stoichiometry number for the synthesis gas passed to the first synthesis reactor to the target value of at least 2 in each case.

In a further example the process is performed at a ratio of the molar flows (n1s/n2s)1 during a first time interval t1 and at a ratio of the molar flows (n1s/n2s)2 during a second time interval t2, wherein the average catalyst activity of the catalyst in the first methanol synthesis reactor is higher during the first time interval than during the second time interval. This makes it possible to react to the changing catalyst activity over time in the at least two serially arranged synthesis reactors over the time intervals t1 and t2 and adjust the stoichiometry number for the synthesis gas passed to the first synthesis reactor to the target value of at least 2 in each case by establishing a ratio of the molar flows (n1s/n2s)1 in the first time interval t1 and a ratio of the molar flows (n1s/n2s)2 during a second time interval t2. The division of the operating duration of the synthesis gas plant into two time intervals is only exemplary and is not to be understood as limiting. It may well be useful to define further time intervals t3, t4 etc. during which further molar flow ratios (n1s/n2s)3, (n1s/n2s)4 etc. are established to allow particularly incremental adjustment of the desired stoichiometry number. However, it should be ensured that the greater control complexity remains acceptable in view of the improved adjustment of the stoichiometry number.

In a further example the process is performed at a ratio of the molar flows (n1s/n2s)1 during a first time interval and at a ratio of the molar flows (n1s/n2s)2 during a second time interval, wherein (n1s/n2s)1 is greater than (n1s/n2s)2.

NUMERICAL EXAMPLES

Simulation calculations for a two-stage methanol synthesis with a water-cooled reactor (WCR, first synthesis reactor) and a gas-cooled reactor (GCR, second synthesis reactor) were performed. The starting material was a simulated natural gas containing 1% by volume $C_2$-hydrocarbons, 1% by volume nitrogen, 1% by volume carbon dioxide, balance methane, which was converted into synthesis gas in a synthesis gas production stage and then sent to methanol synthesis.

After each synthesis stage the methanol product formed was condensed out and a portion of the residual gas remaining in each case was passed as purge gas to a hydrogen recovery apparatus in the form of a PSA plant. The portion of the respective residual gas not discharged as purge gas was passed to the subsequent synthesis stage/recycled to the first synthesis stage. The deactivation of the catalysts in the first and second synthesis reactor was simulated using a mathematical model to illustrate the differences between the first time interval t1 (start of run, SOR) and the second time interval t2 (end of run, EOR). The following target parameters were chosen for SOR and EOR:

Methanol production in each case about 4020 tons per day
Stoichiometry number SN in the WCR 2.9 in each case
Hydrogen loss 1% in each case (as fuel gas)

In order to realize these target parameters during advancing catalyst deactivation it was necessary to establish under SOR conditions (first time interval) a ratio of the purge gas molar flows $(n1s/n2s)_1$ of 2.6 and under EOR conditions (second time interval) a ratio of the purge gas molar flows $(n1s/n2s)_2$ of 0.6.

LIST OF REFERENCE SYMBOLS

1 Process, Plant
10 Conduit
11 Compressor
12 Conduit
16 Mixing apparatus
17 Conduit
18 Conduit
19 Conduit
20 First methanol synthesis reactor
22 Conduit
23 Heat exchanger
24 Conduit
25 Cooler
26 Conduit
30 First phase separation apparatus (liquid separator)
31 Conduit
32 Conduit
34 Conduit
40 Second methanol synthesis reactor
42 Conduit
43 Heat exchanger
44 Conduit
45 Cooler
46 Conduit
50 Second phase separation apparatus (liquid separator)
51 Conduit
52 Conduit
53 Mixing apparatus
54 Conduit
55 Conduit
56 Compressor
60 Hydrogen recovery apparatus
61 Conduit
62 Control valve
63 Conduit
64 Conduit
65 Control valve
66 Conduit
67 Conduit

What is claimed is:

1. A process for producing methanol from a carbon-containing input stream comprising:
   (a) producing a synthesis gas input stream containing hydrogen and carbon oxides using a synthesis gas production process under synthesis gas production conditions from the carbon-containing input stream,
   (b) combining and mixing the synthesis gas input stream with a recycle stream containing hydrogen and carbon oxides to afford a first reactor feed stream,
   (c) introducing the first reactor feed stream into a first methanol synthesis reactor containing at least one catalyst zone comprising a solid, granular catalyst active for methanol synthesis, at least partially converting the first reactor feed stream in the first methanol synthesis reactor under methanol synthesis conditions,
   (d) discharging a first reactor product stream containing methanol and water from the first methanol synthesis reactor, cooling the first reactor product stream below its dew point and supplying the cooled first reactor product stream to a first phase separation apparatus,
   (e) separating the cooled first reactor product stream in the first phase separation apparatus into a first liquid product stream and a first residual gas stream containing unconverted synthesis gas constituents,
   (f) dividing the first residual gas stream into a second reactor feed stream and into a first purge stream,
   (g) introducing the second reactor feed stream into a second methanol synthesis reactor containing at least one catalyst zone comprising a solid, granular catalyst active for methanol synthesis, at least partially converting the second reactor feed stream in the second methanol synthesis reactor under methanol synthesis conditions,
   (h) discharging a second reactor product stream containing methanol and water from the second methanol synthesis reactor, cooling the second reactor product stream below its dew point and supplying the cooled second reactor product stream to a second phase separation apparatus,
   (i) separating the cooled second reactor product stream in the second phase separation apparatus into a second liquid product stream and a second residual gas stream containing unconverted synthesis gas constituents,
   (j) dividing the second residual gas stream into the recycle stream recycled to step (b) and into a second purge stream,
   (k) discharging the first and the second liquid product stream from the process as a crude methanol product stream,
   (l) introducing at least a portion of the first purge stream and at least a portion of the second purge stream into a hydrogen recovery apparatus, separating the first purge stream and the second purge stream in the hydrogen recovery apparatus into a hydrogen-enriched supplementary stream and a hydrogen-depleted third purge stream, and
   (m) recycling at least a portion of the hydrogen-enriched supplementary stream to the first methanol synthesis reactor and discharging the hydrogen-depleted third purge stream from the process.

2. The process according to claim 1, wherein the hydrogen-enriched supplementary stream is mixed with the synthesis gas input stream and/or with the recycle stream before introduction into the first methanol synthesis reactor.

3. The process according to claim 1 wherein the first purge stream and the second purge stream are introduced into a common hydrogen recovery apparatus.

4. The process according to claim 1, wherein the hydrogen recovery apparatus operates according to the principle of pressure swing adsorption and/or according to the principle of membrane separation.

5. The process according to claim 1, wherein the ratio of the molar flows n1s/n2s of the first purge stream n1s to the second purge stream n2s is altered over time.

6. The process according to claim 1, wherein the ratio of the molar flows n1s/n2s of the first purge stream n1s to the second purge stream n2s is altered over time and/or in that the sum of the first purge stream and the second purge stream n1s+n2s is altered over time.

7. The process according to claim 1, wherein the process is performed at a ratio of the molar flows (n1s/n2s)1 during a first time interval t1 and at a ratio of the molar flows (n1s/n2s)2 during a second time interval t2, wherein the average catalyst activity of the catalyst in the first methanol synthesis reactor is higher during the first time interval than during the second time interval.

8. The process according to claim 1, wherein the process is performed at a ratio of the molar flows (n1s/n2s)1 during a first time interval t1 and at a ratio of the molar flows (n1s/n2s)2 during a second time interval t2, wherein (n1s/n2s)1 is greater than (n1s/n2s)2.

9. The process according to claim 8, wherein the first time interval t1 begins with the startup of the process and in that the second time interval t2 ends with the shutdown of the process.

10. The process according to claim 8 wherein the beginning of the first time interval t1 corresponds to the beginning of the catalyst cycle in all methanol synthesis reactors and in that the end of the second time interval t2 corresponds to the end of the catalyst cycle in all methanol synthesis reactors.

11. The process according to claim 8, wherein the ratio of the molar flows (n1s/n2s)1 is greater than 1 and in that the ratio of the molar flows (n1s/n2s)2 is less than 1.

12. The process according to claim 8, wherein the ratio of the molar flows (n1s/n2s)1 is between 1 and 3, and in that the ratio of the molar flows (n1s/n2s)2 is between 0 and 1.

13. The process according to claim 1, wherein the reduction in the molar flow of the first liquid product stream over time serves as a measure for the reduction in catalyst activity of the catalyst in the first methanol synthesis reactor.

14. The process according to claim 1, wherein a temperature measurement apparatus is used to repeatedly measure during performance of the process axial temperature profiles within the catalyst bed in the first methanol synthesis reactor and in that the change in the axial temperature profile over time serves as a measure for the decrease in catalyst activity of the catalyst in the first methanol synthesis reactor.

15. The process according to claim 1, wherein the synthesis gas production process comprises a noncatalytic partial oxidation and/or an autothermal reforming.

16. The process according to claim 1, wherein the stoichiometry number of the synthesis gas input stream is less than 2 and in that the stoichiometry number of the gas mixture obtained from the synthesis gas input stream, the recycle stream and the supplementary stream is more than 2 before introduction thereof into the first methanol synthesis reactor.

* * * * *